(12) United States Patent
Chiou et al.

(10) Patent No.: US 8,697,843 B1
(45) Date of Patent: Apr. 15, 2014

(54) SUPERABSORBANT MATERIALS FROM CHEMICALLY MODIFIED GLUTEN

(71) Applicant: The United States of America, as represented by the Secretary of Agriculture, Washington, DC (US)

(72) Inventors: Bor-Sen Chiou, Albany, CA (US); Trung K. Cao, Vallejo, CA (US); George H. Robertson, Danville, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/763,360

(22) Filed: Feb. 8, 2013

(51) Int. Cl.
*A23J 1/12* (2006.01)
*A23J 3/18* (2006.01)
*C07K 14/415* (2006.01)

(52) U.S. Cl.
USPC .......................................... 530/374; 530/375

(58) Field of Classification Search
None
See application file for complete search history.

(56) References Cited

FOREIGN PATENT DOCUMENTS

EP 2094734 B9 9/2010

OTHER PUBLICATIONS

Gomez-Martinez, D., P. Partial, I. Martinez, and C. Gallegos, "Rheological behaviour and physical properties of controlled-release gluten-based bioplastics" (2009) Bioresource Technology 100:1828-1832.
Reddy, N. Y. Li, and Y. Yang, "Wet Cross-Linking Gliadin Fibers with Citric Acid and a Quantitative Relationship between Cross-linking Conditions and Mechanical Properties" (2009) J. Agric. Food Chem. 57:90-98.
Reddy, N. Y. Li, and Y. Yang, "Alkali-Catalyzed Low Temperature Wet Crosslinking of Plant Proteins Using Carboxylic Acids" (2009) Biotechnol. Prog. 25(1):139-146.
Sessa, D.J. and R.E. Wing, "Thermochemically-modified soybean and corn protein products with enhanced metal-binding properties" (1998) Nahrung 42:266-268.
Sessa, D.J. and R.E. Wing, "Metal chelation of corn protein products/citric acid derivatives generated via reactive extrusion" (1999) Industrial Crops and Products 10:55-63.
Zhang, X. et al., "Biodegration of chemically modified wheat gluten-based natural polymer materials" (2010) Polymer Degradation and Stability 95:2309-2317.
Zohuriaan-Mehr, M. J. and K. Kabiri, "Superabsorbent Polymer Materials: A Review" (2008) Iranian Polymer Journal 17(6):451-477.

*Primary Examiner* — John S Brusca
*Assistant Examiner* — Gerard Lacourciere
(74) *Attorney, Agent, or Firm* — John Fado; Elizabeth R. Sampson; Lesley Shaw (57) ABSTRACT

The present disclosure provides superabsorbent materials comprising wheat gluten chemically modified with citric acid, methods of producing superabsorbent materials and methods of use.

11 Claims, 7 Drawing Sheets

SUPERABSORBANT MATERIALS FROM CHEMICALLY MODIFIED GLUTEN

FIELD OF THE INVENTION

The invention relates to biodegradable superabsorbent materials.

BACKGROUND OF THE INVENTION

Superabsorbent materials can absorb and retain large amounts of a liquid relative to their own mass. Traditionally, superabsorbent materials have been used as an absorbent for water and aqueous solutions for products including e.g., diapers, adult incontinence products, feminine hygiene products, and similar applications.

Unfortunately however, most commercial superabsorbent materials are derived from synthetic monomers, such as acrylic acid and acrylamide. Although these superabsorbent materials can absorb hundreds of times their original weight in water, the use of petroleum-based polymers has several drawbacks. One is that the polymers are produced from a non-renewable resource. Another drawback is that these synthetic polymers are not biodegradable, which leads to persistence and accumulation in the environment.

Thus, there exists a need for completely natural, biodegradable superabsorbent materials. As will be clear from the following disclosure, the present invention provides for this and other needs.

SUMMARY OF THE INVENTION

In one exemplary embodiment, the present invention provides a superabsorbent material comprising gluten chemically modified with citric acid wherein the chemically modified wheat gluten possesses carboxyl groups (COOH) from citric acid. In one exemplary embodiment, the gluten is wheat gluten. In another exemplary embodiment, the COOH from citric acid is present on the gluten at a concentration that is in a range that is between about 3 mmol COOH/g wheat gluten to about 16 mmol COOH/g wheat gluten. In another exemplary embodiment, the chemically modified wheat gluten possesses carboxyl groups from citric acid at a concentration that is about 8 mmol COOH/g wheat gluten. In still another exemplary embodiment, the carboxyl groups are linked to the wheat gluten by way of an ester bond between the citric acid and hydroxyl groups on the wheat gluten.

In another exemplary embodiment, the superabsorbent material absorbs between about 25 times to about 90 times its weight in deionized water. In another exemplary embodiment, the superabsorbent material absorbs about 71 times its weight in deionized water.

In another exemplary embodiment, the invention provides a superabsorbent material comprising wheat gluten and citric acid prepared by: (i) combining wheat gluten and citric acid to form a mixture; (ii) heating the mixture to a temperature between about 100° C. and 150° C.; (iii) mixing, the mixture to react the wheat gluten and citric acid; and (iv) drying the reacted mixture at 55° C. until fully dried.

In one exemplary embodiment, the wheat gluten and citric acid are present in a weight ratio of wheat gluten to citric acid of between about 0.38:1 to about 0.75:1. In another exemplary embodiment, the wheat gluten and citric acid are present in a weight ratio of wheat gluten to citric acid of 0.5:1 and the mixture is heated to 120° C.

In another exemplary embodiment, the invention provides a super absorbent material consisting essentially of wheat gluten and citric acid prepared by: (i) combining wheat gluten and citric acid to form a mixture; (ii) heating the mixture to a temperature between about 100° C. and 150° C.; (iii) mixing, the mixture to react the wheat gluten and citric acid; and (iv) drying the reacted mixture at 55° C. until fully dried. In another exemplary embodiment, the wheat gluten and citric acid are present in a weight ratio of wheat gluten to citric acid of 0.5:1 and the mixture is heated to 120° C.

Other features, objects and advantages of the invention will be apparent from the detailed description which follows.

BRIEF DESCRIPTION OF THE DRAWINGS

FIG. 4 (A) TGA curves of neat and modified wheat gluten samples with a gluten:citric acid ratio of 0.5:1 at different temperatures. (B) Derivative of TGA curves of neat and modified wheat gluten samples with a gluten:citric acid ratio of 0.5:1 at different temperatures FIG. 5 TGA curves of neat and modified wheat gluten samples with different gluten:citric acid ratios at 120° C.

FIG. 6 (A) SEM micrograph of 0.75:1 wheat gluten to citric acid sample heated at 120° C. (B) SEM micrograph of 0.75:1 wheat gluten to citric acid sample heated at 120° C. (C) SEM micrograph of 0.50:1 wheat gluten to citric acid sample heated at 120° C. (D) SEM micrograph of 0.38:1 wheat gluten to citric acid sample heated at 120° C.

DETAILED DESCRIPTION OF THE INVENTION

Definitions

Unless defined otherwise, all technical and scientific terms used herein generally have the same meaning as commonly understood by one of ordinary skill in the art to which this invention belongs.

As used herein, the term "superabsorbent material" as used herein, refers to a material that absorbs and retains large amounts of liquid relative to its own mass and which will not dissolve in the liquid. Typically, a superabsorbent material imbibes or absorbs at least about 10 times its own weight in liquid and retains the imbibed or absorbed liquid under moderate pressure. However, in some exemplary embodiments, a "superabsorbent material" absorbs 25 times to 100 times its weight in liquid wherein the liquid absorbed is an aqueous liquid or an organic liquid. In other exemplary embodiments, a "superabsorbent material" absorbs 25 times to 100 times its weight in deionized water. In some exemplary embodiments, a "superabsorbent material" absorbs 30 times its weight in liquid. In other exemplary embodiments, a "superabsorbent material" absorbs 35 times its weight in liquid. In still other exemplary embodiments, a "superabsorbent material" absorbs 40 times, 50 times, 60 times, 70 times, 80 times, 90 times or more of its weight in liquid.

The term "wheat gluten" as used herein refers to the protein-rich portion of the wheat kernel. Gluten is found only in wheat. As appreciated by a person of ordinary skill in the art, the term "gluten" refers to a composition comprising gliadins and glutenins in different amounts. In some exemplary embodiments, gluten comprises at least about 20% storage proteins derived from prolamine rich cereal such as e.g., wheat. In some exemplary embodiments, the term "gluten" as used herein refers in particular to a composition containing gliadins and glutenins derived from durum wheat. Thus, in some exemplary embodiments, the term "gluten" as used herein refers in to a composition comprising 80% protein wherein 40% of the protein is gliadin. In another exemplary embodiment, the term gluten, refers to the commercially available wheat gluten from a manufacturer, e.g., from Giusto (San Francisco, Calif.).

Corn also has a protein-rich portion, but contains no gluten. However, out of convenience, many people in the corn and other food industries refer to the protein-rich portion from corn as "corn gluten" though it should actually be called "corn protein". Thus, it has become common to call corn storage proteins corn gluten. Although corn may contain prolamins, such as e.g., zein, it does not contain gluten.

The phrase "gluten chemically modified with citric acid" as used herein, refers to gluten wherein at least one hydroxyl group of the gluten has been chemically reacted with citric acid to form an ester bond between the hydroxyl group of the gluten and the citric acid. Thus, "gluten chemically modified with citric acid" is gluten that "possesses carboxyl groups (COOH) from citric acid". As is known in the art, citric acid contains three carboxylic acid groups, each of which can react with hydroxyl groups in gluten. Gluten contains three amino acids, serine, tyrosine, and threonine, that have hydroxyl groups, each of which can react with the carboxylic acid groups in citric acid. Gluten contains 4.3% (w/w) serine, 2.8% (w/w) tyrosine, and 2.4% (w/w) threonine. These amino acids appear in regular repeat units in the gliadin and glutenin chains.

The phrase "absorbs its weight in liquid" as used herein, refers to the ability of a superabsorbent material to absorb a volume of liquid the weight of which is equivalent to the weight of the dry superabsorbent material. Thus, the expression "absorbs about 71 times its weight in liquid" as used herein, refers to the ability of a superabsorbent material to absorb a volume of liquid the weight of which is equivalent to 71 times the weight of the dry superabsorbent material. In an exemplary embodiment, the liquid absorbed by the superabsorbent material is deionized water.

The term "biodegradable" as used herein refers to a composition or substance that decays and becomes absorbed by the environment. A biodegradable substance is capable of decaying through the action of living organisms typically, through the action of living organisms such as bacteria and fungi. Biodegradation of biodegradable substances such as superabsorbent materials as disclosed herein, typically leads to the release of non-toxic components that are recycled by the ecosystem.

The term "isolated" refers to a material that is substantially or essentially free from components which are used to produce the material. For compositions disclosed herein, the term "isolated" refers to material that is substantially or essentially free from components which normally accompany the material in the mixture used to prepare the composition. "Isolated" and "pure" are used interchangeably. Typically, isolated superabsorbent materials have a level of purity that, in exemplary embodiments, is expressed as a range. The lower end of the range of purity for the component is about 60%, about 70% or about 80% and the upper end of the range of purity is about 70%, about 80%, about 90% or more than about 90%. Thus when a superabsorbent material is more than about 90% pure, the purities are also preferably expressed as a range. The lower end of the range of purity is about 90%, about 92%, about 94%, about 96% or about 98%. The upper end of the range of purity is about 92%, about 94%, about 96%, about 98% or about 100% purity. Purity is determined by any art-recognized method of analysis (e.g., HPLC, or a similar means).

I. Introduction

Superabsorbent materials are useful materials by virtue of their ability to imbibe or absorb at least 10 times their own weight in fluid e.g., aqueous fluid, e.g., deionized water. Indeed, some superabsorbent materials can absorb up to 1,000 times their weight in liquid (see e.g., U.S. Pat. No. 3,981,100). Typically, superabsorbent materials are able to retain the imbibed or absorbed fluid under moderate pressure. In contrast, the absorption capacity of common, non-superabsorbent, materials e.g., non-superabsorbent hydrogels, is typically not more that about equal to the weight of the non-superabsorbent material.

Imbibed or absorbed aqueous fluid is taken into the molecular structure of the superabsorbent material rather than being contained in pores from which the fluid can be eliminated by squeezing.

Superabsorbent materials are typically divided into two main classes; e.g., synthetic (petrochemical-based) and natural (e.g., polysaccharide- and polypeptide-based). The natural-based superabsorbent materials are typically prepared through addition of at least some synthetic parts onto the natural substrates, e.g., graft copolymerization of vinyl monomers on polysaccharides and thus are not necessarily free of petrochemical components. That said, most of the current superabsorbents, are produced from acrylic acid (AA), its salts, and acrylamide (AM) via solution or inverse-suspension polymerization techniques. Thus, typical commercial superabsorbent materials are produced from a non-renewable, non-biodegradable materials.

Beginning in the early 1970's, and continuing to the present day, there has been a growing awareness that the continued widespread use of non-biodegradable, petroleum-based polymeric materials may pose serious environmental concerns. These concerns are heightened by production statistics showing the enormous and still-growing volume of non-biodegradable plastics produced annually, the vast majority of which are ultimately interred in landfills. This raises concerns not only as to the amount of space available for solid waste disposal (which is disappearing at an increasingly rapid pace), but also raises equally serious concerns that the leaching of toxic monomers and oligomers from landfilled plastics will contaminate ground water, thereby causing health problems in humans and animals.

In addition to concerns regarding human health and the environment, the world-wide depletion of petroleum reserves, in combination with wildly fluctuating petroleum prices due to political and economic conflicts, indicates that less dependence on petroleum-derived products is prudent. Therefore, the development of alternative, and renewable, resources for industrial products is needed.

Furthermore, because of economic, environmental, and public health concerns accompanying non-biodegradable, petroleum-based products, a non-petroleum-based, environmentally safe, biodegradable, and renewable source for industrial products is needed.

II. Superabsorbent Materials from Chemically Modified Gluten

A. General Methods

Methods disclosed herein utilize routine techniques in the field of chemistry and chemical analysis. Basic texts disclosing the general methods of use in this invention include, e.g.,

*Modern Analytical Chemistry*, by David T. Harvey, McGraw-Hill Science/Engineering/Math (1999); Bell, R. J. *Introductory Fourier Transform Spectroscopy*. New York: Academic Press, 1972.

B. Gluten

Grain proteins, such as those derived from wheat or corn gluten, are commercially available and are relatively inexpensive in comparison to other biomaterials and many synthetic polymers. Gluten is well known in the art (see e.g., Delcour, J. A., et al. (2012) Annu. Rev. Food Sci Technol. 3:469-492). Gluten is a protein by-product of the starch fabrication and is found in e.g., wheat, barley, rye, malts and triticale. Thus, it is readily available in high quantity and at low cost.

As is well known in the art, gluten typically comprises two main groups of proteins, gliadin and glutenin. Gliadins are monomeric glycoproteins which contain disulphide bonds. As is well known in the art, gliadins can be separated into four groups, alpha-, beta-, gamma- and omega-gliadins. They have low molecular weight and a low level of aminoacids with charged side groups and a are slightly soluble in ethanol. The glutenins, in contrast, are protein aggregates of high molecular weight (HMW) and low molecular weight (LMW) subunits with molar masses from about 200,000 to a few million, which are stabilized by intermolecular disulfide bonds, hydrophobic interactions and other forces and have a three dimensional structure. Their molecular weight is typically at least ten times higher than that of gliadins. Glutenin (also called glutelin or glutenine) is the major protein within wheat flour, typically making up about 47% of the total protein content.

Wheat gluten materials have the fastest degradation rates. Gluten is fully biodegradable and the products obtained are non-toxic.

1. Chemical Modification of Gluten

In an exemplary embodiment, the invention provides a superabsorbent material comprising gluten chemically modified with citric acid. Briefly, to prepare a superabsorbent material the sample is first coated with citric acid and then heated to temperatures above 100° C. In one exemplary embodiment, a sample comprising gluten and citric acid at a 0.5:1 gluten:citric acid ratio is reacted at 120° C. to prepare a superabsorbent material. In reacting with gluten, two carboxylic acid groups on citric acid form an anhydride through loss of a water molecule. The anhydride then reacts with hydroxyl groups on the polysaccharide or protein to form an ester linkage (see e.g., FIG. 1). After reacting the citric acid with the gluten, the reaction is neutralized, washed with acetone and allowed to settle.

Unmodified gluten can absorb about twice its weight in water. However, after chemical modification with citric acid as disclosed herein, chemically modified gluten (e.g., wheat gluten) is able to absorb about 25 times to 100 times its weight in liquid (e.g., deionized water).

It is typically the case that, adding more citric acid to the modification reaction results in chemically modified gluten which is modified to a greater extent. Similarly, in general, the temperature at which the modification reaction is conducted influences the amount of modification which occurs and increased temperature results in chemically modified gluten which is modified to a greater extent.

Although increased amounts of citric acid and increasing temperatures result in chemically modified gluten which is modified to a greater extent, as disclosed herein more extensive modification does not necessarily lead to a superabsorbent material with increased water uptake ability. Indeed, without being bound by theory it is believed that the best water uptake values are an optimal balance between number of introduced carboxyl groups and number of additional cross-links introduced during the reaction of gluten and citric acid. This can be seen e.g., in Table 1 and Table 2 in Example 1. In Table 1, the 0.38:1 gluten:citric acid sample at 120° C. has the highest degree of reaction with citric acid, but as shown in Table 2, does not have the greatest ability to absorb water. Thus, without being bound by theory, it is believed that the introduction of more cross-links and the correspondingly higher cross-link density ultimately leads to lower water uptake since the cross-links restrict swelling of the gluten chains.

The amount of citric acid reacted with the gluten can be determined by any method known in the art. In one exemplary embodiment, titration is used to determine the amount of citric acid that reacted with the gluten. In other exemplary embodiments, 2-D electrophoresis, FTIR (see e.g., Sessa, D. J.; Wing, R. E. Nahrung 1998, 42(3/4), 266; Coma, V.; Sebti, I.; Pardon, P.; Pichavant, F. H.; Deschamps, A. Carbohydr Polym 2003, 51, 265; Demitri, C.; Del Sole, R.; Scalera, F.; Sannino, A.; Vasapollo, G.; Ambrosio, L.; Nicolais, L. J Appl Polym Sci 2008, 110, 2453; Salam, A.; Pawlak, J. J.; Venditti, R. A.; El-Tahlawy, K. Biomacromolecules 2010, 11(6), 1453; Salam, A.; Pawlak, J. J.; Venditti, R. A.; El-Tahlawy, K. Cellulose 2011, 18, 1033; Salam, A.; Venditti, R. A.; Pawlak, J. J.; El-Tahlawy, K. Carbohydr Polym 2011, 84, 1221; Gorgieva, S.; Kokol, V. Carbohydr Polym 2011, 85, 664), or NMR (see e.g., Salam, A.; Pawlak, J. J.; Venditti, R. A.; El-Tahlawy, K. Biomacromolecules 2010, 11(6), 1453) is used to determine the amount of citric acid that reacted with the gluten.

III. Uses for Superabsorbent Materials from Chemically Modified Wheat Gluten

Superabsorbent materials as disclosed herein find numerous uses. In some exemplary embodiments superabsorbent materials as disclosed herein are useful in soil applications to improve water retention, decrease soil crusting, decrease irrigation requirements, provide for earlier seed germination and earlier blooming, etc. Soil application of superabsorbent materials as disclosed herein also improves soil water holding capacity, soil water availability, soil infiltration, aeration, friability, flocculation etc. and may reduce impact pressure in turf (injury), reduce pesticide (herbicides, fungicides) use, absorbs soluble fertilizer and time releases it, improves drainage when used as a soil amendment. In an exemplary embodiment, superabsorbent materials comprising gluten citrate as disclosed herein are well suited for soil applications as they are biodegradable and need not be removed after use. In other exemplary embodiments superabsorbent materials comprising gluten citrate as disclosed herein are useful as rheology modifiers in food products. In one exemplary embodiment, gluten citrate superabsorbents are used as rheology modifiers to increase solution viscocity. In another exemplary embodiment, gluten citrate superabsorbents are used as rheology modifiers to promote moisture retention in bakery products.

Direct application to a seed or root to improve germination/blooming etc or as a rooting medium.

In other exemplary embodiments, superabsorbent materials as disclosed herein are useful in diapers, adult incontinence products, feminine hygiene products, and similar applications.

In still other exemplary embodiments, superabsorbent materials as disclosed herein are useful in medical applications, such e.g., as wound dressings and gauzes, to absorb body fluids. In still other exemplary embodiments, since it is food grade, gluten citrate can be used in food applications, such as rheology modifiers to increase solution viscosity and moisture retention agents in bakery products.

The following examples are offered to illustrate, but not to limit the invention.

EXAMPLES

Example 1

The following Example illustrates an exemplary method for preparation and characterization of chemically modified wheat gluten possessing carboxyl groups from citric acid.

Experimental

Reaction of Wheat Gluten with Citric Acid

Figure 1:
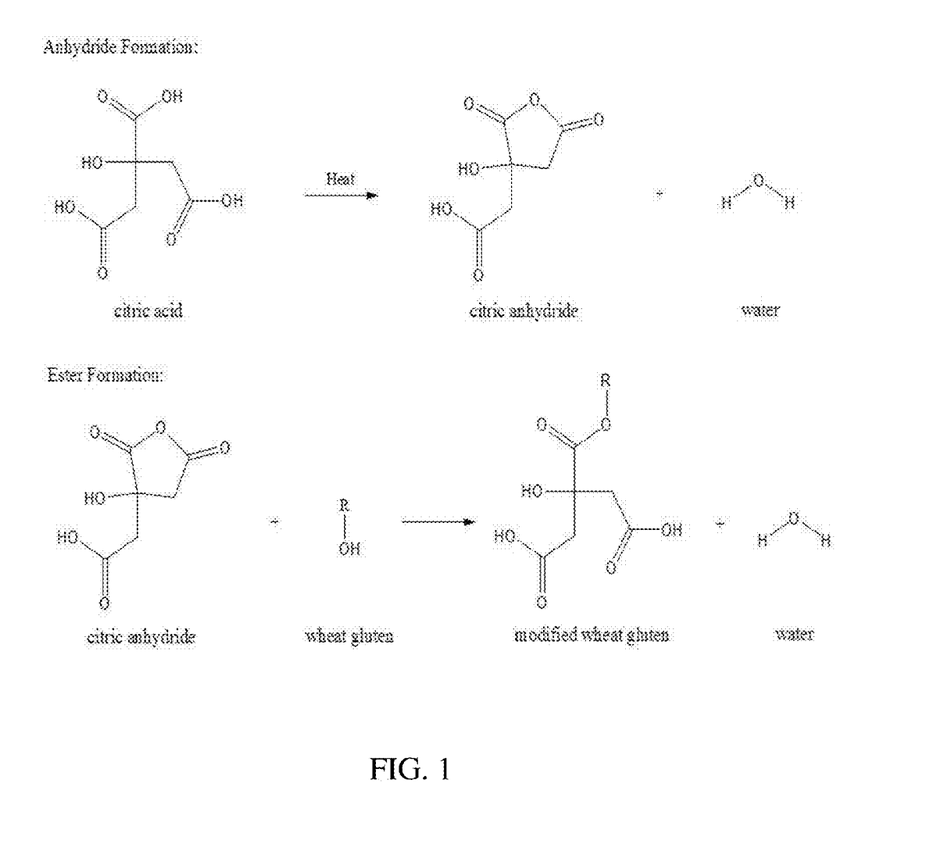
FIG. 1 Schematic representation of reaction mechanism of wheat gluten with citric acid.

A Hobart mixer (model N50A, Troy, Ohio) was used to blend wheat gluten (Giusto, San Francisco, Calif.) with deionized water in a 1:2 ratio for five minutes. A 6.93 M citric acid (Sigma-Aldrich, St. Louis, Mo.) solution was then slowly added during the blending process for another 30 minutes. Citric acid solution was added to produce samples containing wheat gluten to citric acid in weight ratios of 0.38:1, 0.50:1, and 0.75:1. After mixing, the sample was placed in a 55° C. oven for up to five days until it became fully dried. During the drying process, the sample was broken into smaller pieces each day to improve drying efficiency. A mill with a one mm size screen was then used to grind the dried sample. The sample was heated in vacuo for 30 minutes to react citric acid with gluten. The oven temperatures were set at 100, 110, 120, and 130° C. during reaction. A schematic of the reaction of citric acid with gluten is shown in FIG. 1. When citric acid was heated, it dehydrated to form an anhydride. The anhydride then reacted with hydroxyl groups on gluten amino acids, such as serine and tyrosine, to form gluten citrate and water. After reaction, the sample (10 g) was mixed with 200 ml deionized water. This mixture was neutralized to a pH (Hach Sension1 pH meter, Loveland, Colo.) of 7.0 using a 0.4 M NaOH (Sigma-Aldrich) solution. The sample was then rinsed with 500 ml deionized water and filtered using Whatman (Piscataway, N.J.) no. 4 filter paper. After this, the sample was rinsed with 400 ml acetone (Fisher Scientific, Pittsburgh, Pa.) and allowed to settle before the acetone was decanted. This acetone rinse was repeated three times.

Titration to Determine Amount of Citric Acid Reacted

Titration was performed on the modified gluten samples after the gluten had been reacted with citric acid in the oven. After reaction, the modified sample was mixed with 200 ml deionized water using a stir bar. The mixing was stopped after the pH reading became stable. The gluten was then allowed to settle and 25 ml of supernatant was decanted to a separate container. The supernatant was neutralized to a pH of 7.0 with a 0.4 M NaOH solution. The amount of NaOH solution required for neutralization indicated the amount of unreacted citric acid.

Fourier Transform Infrared Spectroscopy

A Perkin Elmer 2000 FTIR spectrometer (Waltham, Mass.) was used to characterize the chemical composition of the gluten samples. The samples were ground into powder with a ball mill and placed in a DuraSamplIR attenuated total reflectance attachment (ASI SensIR Technology, Danbury, Conn.). Each IR spectrum contained an average of 50 scans over a ten minute period with a resolution of 4 cm−1.

Thermogravimetric Analysis

A TA Instruments TGA 2950 (New Castle, Del.) was used to characterize the thermal stability of the gluten samples. Each 11 mg sample was heated from 30° C. to 800° C. at a rate of 10° C./min. The sample was maintained in a nitrogen atmosphere by using a nitrogen gas flow rate of 40 cm³/min. Each sample was conditioned in a 50% relative humidity chamber for at least 48 hours before the test. The humidity was maintained in the chamber by using a saturated solution of calcium nitrate tetrahydrate ($Ca(NO_3)_2 \cdot 4H_2O$; Fisher Scientific) in deionized water.

Scanning Electron Microscopy

Wheat gluten samples were affixed to stubs with carbon adhesives. A Polaron (Hatfield, Pa.) E5100 Sputter Coater was then used to apply a gold coating at a voltage of 1.5 kV and a discharge current of 20 mA for 90 seconds. The vacuum chamber in the sputter coater was set to a pressure of 10 Pa. A Hitachi (Pleasanton, Calif.) S-4700 Scanning Electron Microscope (SEM) was used to observe the samples under ×1.00 k and ×5.00 k magnifications. The voltage setting was 15.0 kV and the current setting was 10 μA.

Water Uptake

Each gluten sample (0.5 g) was mixed with 50 ml of deionized water. After two hours, the sample was vacuum filtered until no water dripped through the filter. The sample was then placed in a Denver Instrument IR-200 moisture analyzer (Bohemia, N.Y.) and heated to 115° C. until the sample weight remained constant. Water uptake was calculated as:

$$W = \frac{m_H - m_D}{m_D} \quad (1)$$

where W is water uptake (g of water/g dry gluten), $m_H$ is initial mass of the hydrated sample, and $m_D$ is mass of the dry sample.

Results

FTIR Spectroscopy

Figure 2:
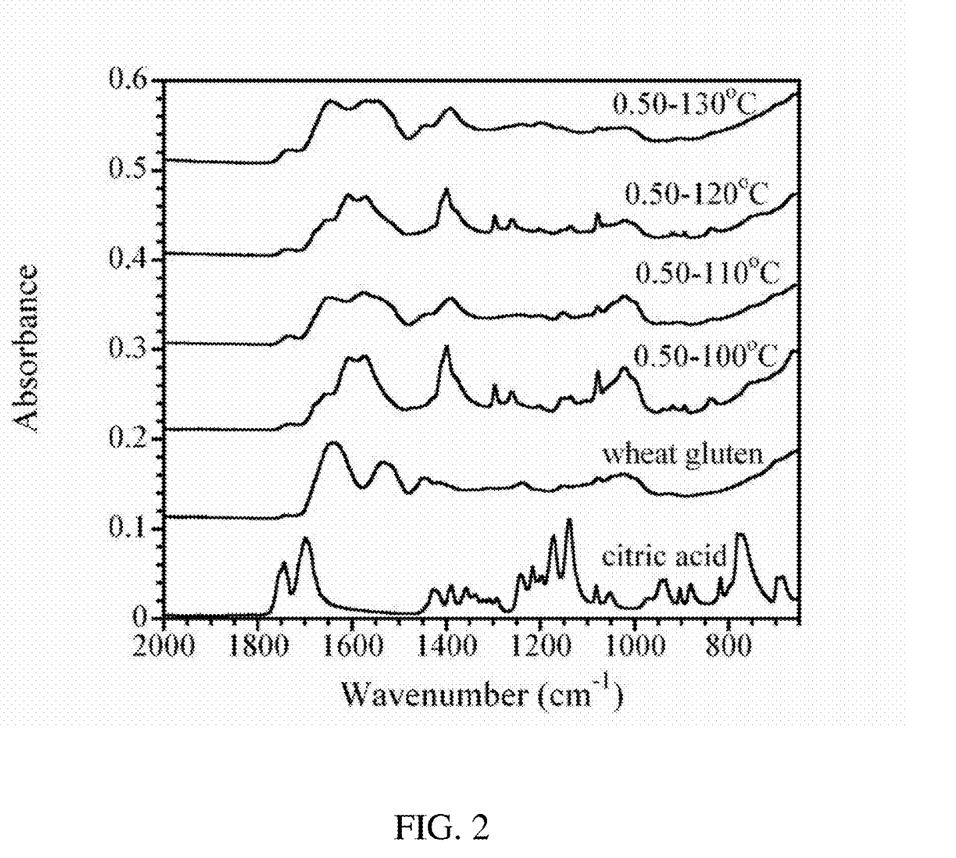
FIG. 2 FTIR spectra of citric acid, wheat gluten, and modified wheat gluten samples with gluten:citric acid ratio of 0.5:1 at different reaction temperatures. Each spectrum has been shifted up 0.1 absorbance units from the one below it.

The acid modified samples showed the presence of carboxylate (—CO2-) groups, which were not present in neat gluten. This is shown in FIG. 2. FIG. 2 shows a plot of the FTIR spectra of citric acid, neat gluten, and modified gluten with different gluten to citric acid ratios. As can be seen in FIG. 2, the neat gluten sample contained the amide I (1639 cm−1) and amide II (1533 cm−1) peaks. After reacting with citric acid, all samples showed asymmetric —CO2- stretching (1608 cm−1) and symmetric —CO2- stretching (1399 cm−1) peaks. Also, modified gluten samples contained saturated aliphatic ester (C=O) stretching vibrations at 1730 cm−1. This indicated citric acid had reacted with hydroxyl groups on gluten to form ester linkages (see e.g., FIG. 1).

Figure 3:
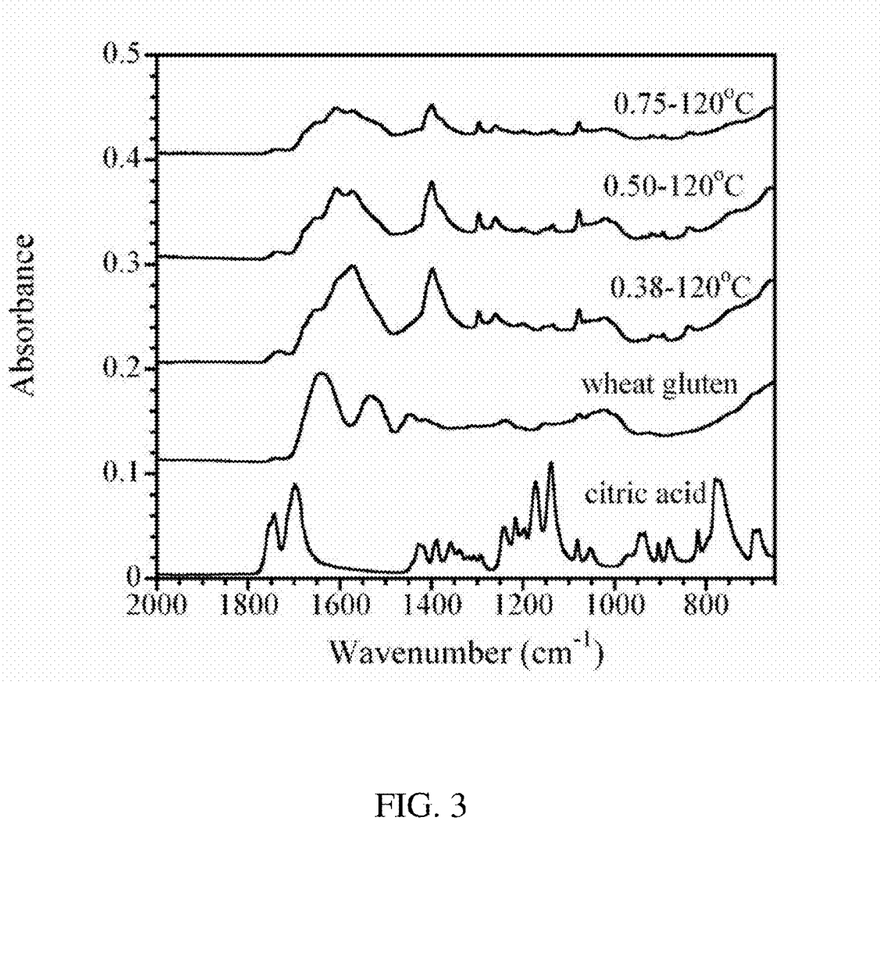
FIG. 3 FTIR spectra of citric acid, wheat gluten, and modified wheat gluten samples with different gluten:citric acid ratios at 120° C. Each spectrum has been shifted up 0.1 absorbance units from the one below it.

All samples reacted at different temperatures also contained carboxylate group stretching vibrations at 1608 cm−1 and 1399 cm−1 as well as ester group stretching vibrations at 1730 cm−1. This is shown in FIG. 3. FIG. 3 shows a plot of the FTIR spectra of 0.50:1 samples reacted between 100° C. and 130° C. The presence of carboxylate and ester groups indicated citric acid reacted with hydroxyl groups on gluten within the experimental temperature range.

Titration Results

More citric acid reacted with gluten at higher reaction temperatures. This is shown below in Table 1. The addition of more citric acid (lower gluten:citric acid ratio) also resulted in an increase of citric acid reacted with gluten (Table 1). These results applied to reactions at both 110° C. and 120° C.

TABLE 1

Citric acid reaction with wheat gluten

| Gluten:Citric Acid Ratio | mmol citric acid reacted/g wheat gluten | | | |
|---|---|---|---|---|
| | 100° C. | 110° C. | 120° C. | 130° C. |
| 0.38:1 | | | 6.7 ± 1.1 | |
| 0.50:1 | 3.8 ± 1 | 5.0 ± 0.2 | 4.1 ± 0.6 | 5.9 ± 1 |
| 0.75:1 | | 3.6 ± 0.9 | 4.0 ± 0.9 | |

Thermal Stability

Figure 4A:
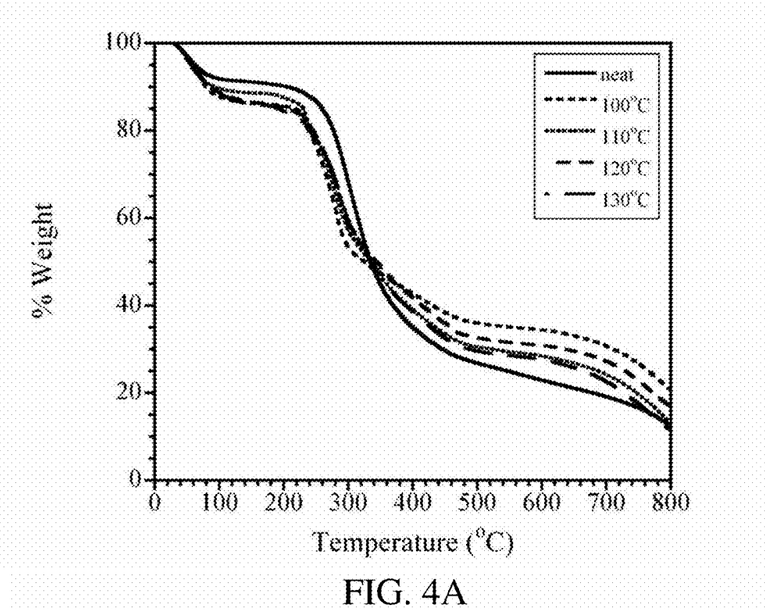

The modified wheat gluten samples at different reaction temperatures were less thermally stable than the neat gluten sample. This is shown in FIG. 4A. As can be seen in FIG. 4A, all samples exhibited two main decreases in their mass during heating. The first one occurred at 100° C., which indicated loss of water. All the modified gluten samples had greater water loss than the neat sample due to higher equilibrium moisture contents. After this point, the modified gluten samples had rapid decreases in weight at a temperature range of 225-234° C. In comparison, the neat gluten sample began to rapidly decrease in weight at approximately 250° C. due to degradation of gluten. These results indicate lower thermal stability of carboxylate groups in the modified samples.

Figure 4B:
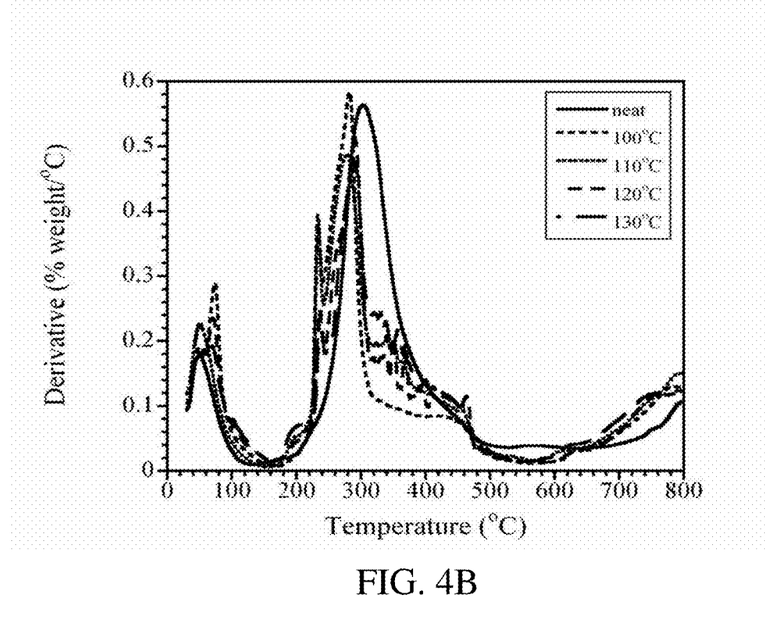

The lower thermal stability of the modified gluten samples can also be seen in the derivatives of their weight loss, which are shown in FIG. 4B. All the modified gluten samples exhibited an increase in their derivative values at lower temperatures than the neat gluten sample. Also, the derivative curves for the modified samples had more jagged peaks than that of the neat sample. This indicated that more heterogeneous structures were present in the modified samples.

Figure 5:
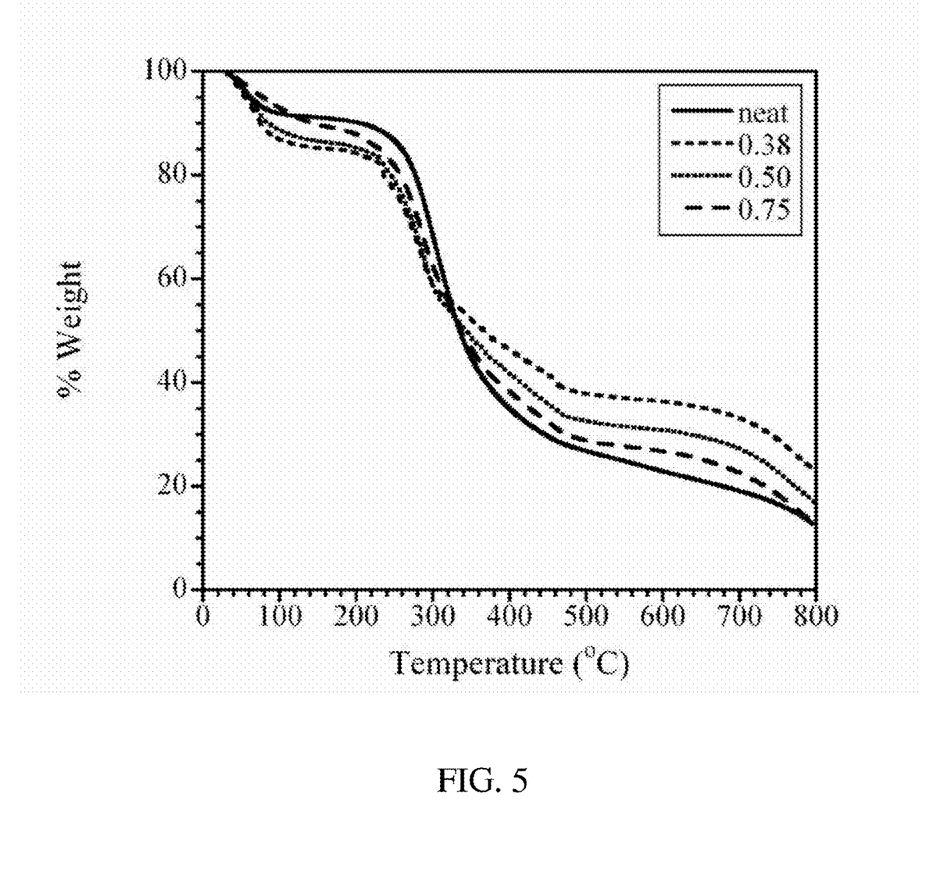
Figure 6A:
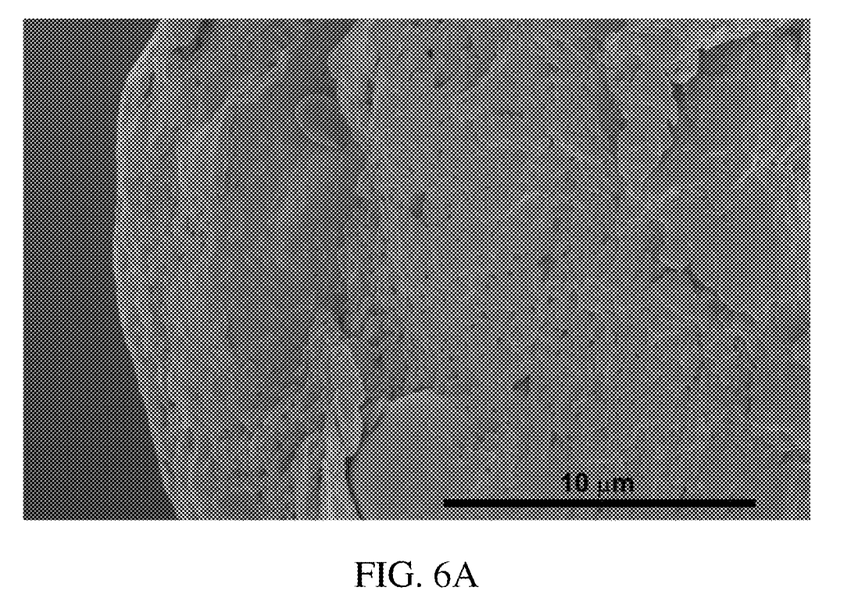
Figure 6B:
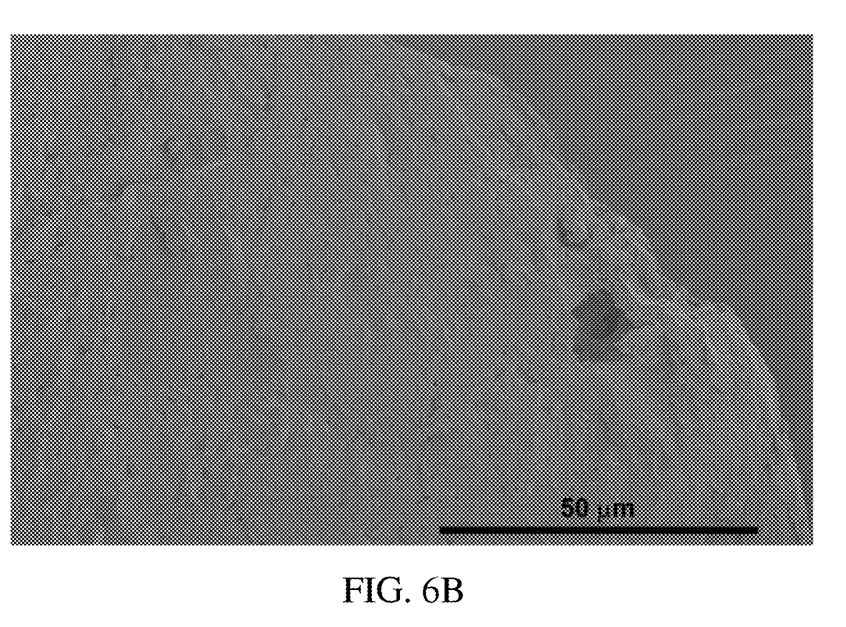
Figure 6C:
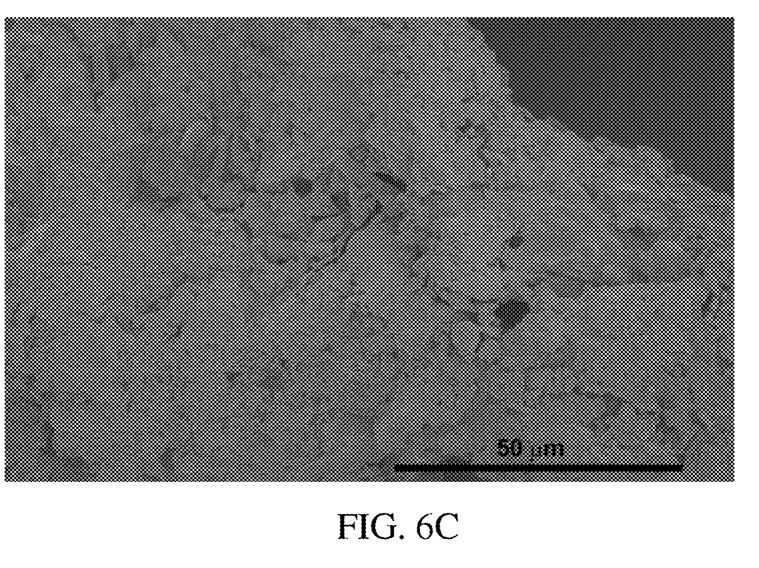
Figure 6D:
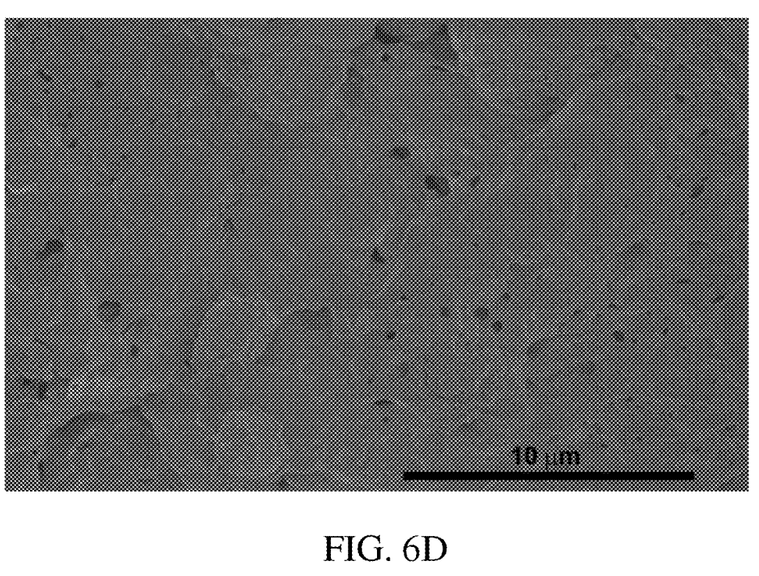

The modified gluten samples with various gluten:citric acid ratios were also less thermally stable than the neat gluten sample. This is shown in FIG. 5. All the modified gluten samples had higher equilibrium moisture levels than the neat gluten sample. Also, the modified samples with gluten:citric acid ratios of 0.38:1 and 0.75:1 showed rapid weight loss at a temperature range of 229-235° C., similar to the samples with gluten:citric acid ratio of 0.50:1 reacted at different temperatures (see e.g., FIG. 4A). In addition, the derivative curves of the samples with different gluten:citric acid ratios also had jagged peaks, indicating heterogeneous structures (data not shown).

Scanning Electron Microscopy

The citric acid modification did not effect surface features of wheat gluten samples. This is shown in FIG. 6, which presents SEM micrographs of neat and modified gluten samples at different gluten to citric acid ratios. The neat gluten sample had a relatively rough surface and contained pores of various sizes. The modified gluten samples also had similar features, indicating the citric acid treatment did not alter surface morphology to a large extent.

Water Uptake

The modified gluten samples were able to absorb up to 71 times their weight in deionized water. This is shown below in Table 2.

TABLE 2

Water uptake of modified wheat gluten

| Gluten:Citric Acid Ratio | Water Uptake | | | |
|---|---|---|---|---|
| | 100° C | 110° C | 120° C | 130° C |
| 0.38:1 | | | 45 ± 14 | |
| 0.50:1 | 32 ± 21 | 68 ± 19 | 71 ± 20 | 50 ± 20 |
| 0.75:1 | | 37 ± 17 | 27 ± 2 | |

Neat gluten has a water uptake value of 1.5. This increase in water uptake of modified gluten was believed to be due to the attachment of carboxylic acid groups onto gluten from reaction with citric acid. After neutralization with sodium hydroxide, the carboxylic acid groups loose a proton to become carboxylate groups. Without being bound by theory it is believed that the negatively charged carboxylate groups repel each other within the wheat gluten matrix. When the gluten sample is placed in water, the gluten chains begin to swell due to absorbance of water. The repulsion between the carboxylate groups forces the gluten matrix to swell even further, allowing for more incorporation of water. Eventually, swelling stops due to restrictions in movement of gluten chains from disulfide cross-links existing in the wheat gluten molecule(s).

In these experiments, a gluten to citric acid ratio of 0.50:1 and a reaction temperature of 120° C. resulted in the highest water uptake value of 71. This is shown in Table 2. The 0.50:1 sample reacted at 110° C. also had a comparable water uptake value.

For gluten samples in this study, the 0.50:1 sample at 130° C. and the 0.38:1 sample at 120° C. contained the largest amount of reacted citric acid (see Table 1). However, this increase in citric acid reaction did not result in the highest water uptake values. Without being bound by theory, it is believed that this result could be due to more cross-linking in these samples, leading to an increase in cross-link density and lower swelling capacity when placed in water. Accordingly, the lower swelling capacity would reduce water uptake, which was consistent with the results in Table 2.

Example 2

The following Example illustrates that modification of "corn gluten" with citric acid does not produce superabsorbent materials.

Attempts were made to modify corn gluten (zein) with citric acid using the methods as disclosed hereinabove in Example 1. However modification of corn gluten with citric acid did not produce superabsorbent materials. Without being bound by theory, it is believed this could be due to the disulfide cross-links present in wheat gluten that are not present in corn gluten.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A superabsorbent material comprising wheat gluten chemically modified with citric acid wherein the chemically modified wheat gluten possesses carboxyl groups (COOH) from citric acid.

2. The superabsorbent material of claim 1, wherein the COOH from citric acid is present on the wheat gluten at a concentration that is in a range that is between about 3 mmol COOH/g wheat gluten to about 16 mmol COOH/g wheat gluten.

3. The superabsorbent material of claim 1, wherein the chemically modified wheat gluten possesses carboxyl groups from citric acid at a concentration that is about 8 mmol COOH/g wheat gluten.

4. The superabsorbent material of claim 1, wherein the carboxyl groups are linked to the wheat gluten by way of an ester bond between the citric acid and hydroxyl groups on the wheat gluten.

5. The superabsorbent material of claim 1, wherein the superabsorbent material absorbs between about 25 times to about 90 times its weight in deionized water.

6. The superabsorbent material of claim 5, wherein the superabsorbent material absorbs about 71 times its weight in deionized water.

7. A super absorbent material comprising wheat gluten and citric acid prepared by:
(i) combining wheat gluten and citric acid;
(ii) mixing the gluten and citric acid to provide a homogeneous mixture;
(iii) drying the homogeneous mixture at a temperature≤65° C. until fully dried to provide a dried mixture;
(iv) grinding the dried mixture to provide a ground dried mixture;
(v) heating the ground dried mixture in vacuo at a temperature that is in a range that is between about 100° C. and about 150° C. to react the wheat gluten and citric acid and provide a reacted mixture;
(vi) mixing the reacted mixture with water;
(vii) neutralizing the reacted mixture to achieve a neutralized reacted mixture having a pH of about 7;
(viii) filtering the neutralized reacted mixture to collect the neutralized reacted mixture; and
(ix) rinsing the collected neutralized reacted mixture with acetone.

8. The superabsorbent material of claim 7, wherein the wheat gluten and citric acid are present in a weight ratio of wheat gluten to citric acid of between about 0.38:1 to about 0.75:1.

9. The superabsorbent material of claim 8 wherein the wheat gluten and citric acid are present in a weight ratio of wheat gluten to citric acid of 0.5:1 and the mixture is heated to 120° C.

10. A super absorbent material consisting essentially of wheat gluten and citric acid prepared by:
(i) combining wheat gluten and citric acid;
(ii) mixing the gluten and citric acid to provide a homogeneous mixture;
(iii) drying the homogeneous mixture at a temperature≤65° C. until fully dried to provide a dried mixture;
(iv) grinding the dried mixture to provide a ground dried mixture;
(v) heating the ground dried mixture in vacuo at a temperature that is in a range that is between about 100° C. and about 150° C. to react the wheat gluten and citric acid and provide a reacted mixture;
(vi) mixing the reacted mixture with water;
(vii) neutralizing the reacted mixture to achieve a neutralized reacted mixture having a pH of about 7;
(viii) filtering the neutralized reacted mixture to collect the neutralized reacted mixture; and
(ix) rinsing the collected neutralized reacted mixture with acetone.

11. The superabsorbent material of claim 10 wherein the wheat gluten and citric acid are present in a weight ratio of wheat gluten to citric acid of 0.5:1 and the mixture is heated to 120° C.

\* \* \* \* \*